United States Patent [19]

Callahan et al.

[11] Patent Number: 5,470,849
[45] Date of Patent: Nov. 28, 1995

[54] γ-TURN PEPTIDOMIMETICS AS FIBRINOGEN ANTAGONISTS

[75] Inventors: James F. Callahan, Philadelphia; William F. Huffman, Malvern, both of Pa.

[73] Assignee: SmithKline Beecham Corp., Philadelphia, Pa.

[21] Appl. No.: 50,178

[22] PCT Filed: Oct. 31, 1991

[86] PCT No.: PCT/US91/08166

§ 371 Date: Apr. 30, 1993

§ 102(e) Date: Apr. 30, 1993

[51] Int. Cl.⁶ .............. A61K 31/55; C07D 401/00; C07D 405/00; C07D 409/00

[52] U.S. Cl. .......... 514/212; 540/524; 540/531; 540/533; 540/596; 540/597; 540/602; 540/603; 540/609; 540/610

[58] Field of Search .............. 514/212; 540/531, 540/533, 524, 596, 597, 602, 603, 609, 610

[56] References Cited

U.S. PATENT DOCUMENTS

| | | | |
|---|---|---|---|
| 4,315,024 | 2/1982 | Abelson | 424/273 R |
| 4,831,135 | 5/1989 | Crews et al. | 540/524 |
| 4,966,911 | 10/1990 | Clark et al. | 514/385 |
| 5,001,113 | 3/1991 | Williams et al. | 540/531 |
| 5,075,302 | 12/1991 | Neustadt | 514/212 |
| 5,296,489 | 3/1994 | Donald et al. | 514/291 |
| 5,302,591 | 4/1994 | Fletcher et al. | 512/221 |

*Primary Examiner*—Robert T. Bond
*Attorney, Agent, or Firm*—Charles M. Kinzig; Stephen Venetianer; Edward T. Lentz

[57] ABSTRACT

This invention relates to a method of inhibiting platelet aggregation, and compounds which are mimics of the peptide sequence Arg-Gly-Asp.

16 Claims, No Drawings

γ-TURN PEPTIDOMIMETICS AS FIBRINOGEN ANTAGONISTS

FIELD OF THE INVENTION

This invention relates to novel compounds which inhibit platelet aggregation, pharmaceutical compositions containing the compounds and methods of using the compounds for inhibiting platelet aggregation. A method of using the compounds of this invention in combination with fibrinolytic agents is also disclosed.

BACKGROUND OF THE INVENTION

A thrombus is the result of processes which initiate the coagulation cascade. It is composed of an aggregation of platelets enmeshed in a polymeric network of fibrin. This process is normally initiated as a consequence of tissue injury and has the effect of slowing or preventing blood flow in a vessel. Etiological factors which are not directly related to tissue injury, such as atherosclerotic plaque, inflammation of the blood vessels (phlebitis) and septicemia, may also initiate thrombus formation. In some instances, the inappropriate formation of a thrombus, and subsequent decrease in blood flow, may have pathological consequences, such as stroke, pulmonary embolism and heart disease.

Platelets play a major role in thrombus formation. Current antithrombotic therapy employs agents that modify the platelet/endothelial cell arachidonate-prostaglandin system, such as prostacyclin analogues, cyclooxygenase inhibitors, thromboxane synthesis inhibitors and thromboxane receptor antagonists; and anti-coagulants, such as heparin. These agents inhibit one or both of two discernible phases of platelet aggregation. The primary phase, which is a response to chemical stimuli, such as ADP (adenosine diphosphate), collagen, epinephrine or thrombin, causes initial activation of the platelets. This is followed by a secondary phase, which is initiated by the platelets themselves, and is characterized by thromboxane $A_2$ ($TxA_2$) synthesis and the release of additional ADP from platelet storage granules, which further activates platelets.

Platelet aggregation is believed to be mediated primarily through the GPIIb-IIIa platelet receptor complex. Von Willebrand factor, a plasma protein, and fibrinogen are able to bind and crosslink GPIIb-IIIa receptors on adjacent platelets and thereby effect aggregation of platelets. Fibronectin, vitronectin and thrombospondin are proteins which have also been demonstrated to bind to GPIIb-IIIa. These proteins, all of which contain an Arg-Gly-Asp peptide sequence, are believed to be members of a superfamily of molecules which mediate cellular adhesion and attachment reactions. Fibronectin, for instance, is found in plasma and as a structural protein in the intracellular matrix. Binding between the structural proteins and GPIIb-IIIa may function to cause platelets to adhere to damaged vessel walls.

Nievelstein et al. (*Thromb, and Hemostasis*, 58, 2133(1987)) have reported that -RGDS- peptides inhibit thrombin induced aggregation and adhesion of platelets to fibronectin, and may interact through the GPIIb-IIIa complex. U.S. Pat. No. 4,683,291 discloses peptides containing Arg and Lys and an -RGD- sequence which inhibit binding of fibrinogen to platelets and inhibit platelet aggregation. Tetrapeptides which contain the sequence X-Gly-Asp-, wherein X is a guanidine-containing aliphatic carboxylic acid or amino acid residue, are disclosed in EP-A 0 319 506 as inhibitors of platelet aggregation. EP-A 0 275 748 discloses linear tetra- to hexapeptides and cyclic hexapeptides which bind to the GPIIb-IIIa receptor and inhibit platelet aggregation. Other peptides and polypeptides which contain an RGD sequence and inhibit fibrinogen binding are disclosed by Plow et al., *Blood*, 70, 110 (1987), Ginsberg et al., *J. Biol. Chem.*, 260, 3931 (1985), Ruggeri et al., *Proc. Natl. Acad. Sci.*, 83, 5708 (1986) and Haverstick et al., *Blood*, 66, 946 (1985). Linear and cyclic peptides, the disclosure of which are incorporated herein by reference, are reported in EP-A 0 341 916. There is a need for new molecules which inhibit the binding of GPIIb-IIIa to fibrinogen and inhibit platelet aggregation.

Molecules which mimic a γ-turn in a peptide have been disclosed in attempts to elucidate the biologically active conformation of enkephalin and its analogues. In particular compounds of the formula (I):

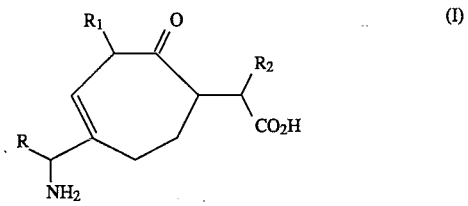

wherein R and $R_1$ are H or benzyl and $R_2$ is H, benzyl or isobutyl, have been disclosed by Huffman et al., Peptides: Chemistry and Biology, Proceedings of the Tenth American Peptide Symposium, Marshall, G. ed., ESCOM, Leiden, 105 (1988). Similar compounds employing a γ-turn mimic have been disclosed by Huffman et al., Synthetic Peptides: Approaches to Biological Problems., UCLA Symposium on Molecular and Cellular Biology, 86, Tam, J. and Kaiser, T. ed., Alan R. Liss, Inc., New York, 257 (1989). These studies concluded that analogues containing these γ-turn mimics did not conform to the biologically active conformation of leucine enkephalin.

It has now been discovered that molecules which mimic the Arg-Gly-Asp sequence and constrain it into a putative γ-turn are useful inhibitors of fibrinogen-GPIIb-IIIa binding and platelet aggregation.

Recent advances for treatment of occluded arteries and deep vein thrombosis employ fibrinolytic agents to lyse thrombi or emboli in order to reestablish or improve blood flow. Fibrinolytic agents, such as anistreplase, tissue plasminogen activator (tPA), urokinase (UK), pro-Urokinase(pUK), and streptokinase (SK), and mutants and derivatives thereof, are proteolytic enzymes which cause fibrin to be hydrolyzed at specific sites and thereby fragment the fibrin network. Lysis of fibrin into smaller peptides has the effect of solubilizing the thrombus or embolus. A recurrent problem with such therapy, however, is the reocclusion of the blood vessel due to formation of a secondary thrombus.

Fibrinolytic therapy is most commonly used for re-establishing flow in a thrombosed blood vessel. However, fibrinolytic therapy does not reverse the factors responsible for the initiation of the thrombus. For this reason, anticoagulants such as heparin are often used to prevent reocclusion. In fact, patients which have a high degree of stenosis in an artery are at extremely high risk of rethrombosis after reperfusion, even in the presence of high doses of heparin. See Gold et al., *Circ.*, 73, 347–52 (1986). In addition, use of SK and tPA has been associated with platelet hyperaggregability. See Ohlstein, et al., *Thromb. Res.*, 4, 575–85 (1987). Treatment with higher doses of tPA can be associated with systemic bleeding and is not recommended for preventing reocclusion. There is, therefore, a need for a method for preventing rethrombosis after fibrinolytic therapy.

EP-A 0 368 232 discloses TxA$_2$ antagonists for use in a method for inhibiting reocclusion following reperfusion and for lowering the dose of tPA required for fibrinolysis. Yasuda et al. (*Clin. Res.*, 34, 2 (1986)) have demonstrated that reocclusion by fibrin rich platelet thrombi, after thrombolysis with tPA, may be inhibited by a murine monoclonal antibody to GPIIb-IIIa in dogs. This invention discloses a new method for inhibiting reocclusion of a blood vessel by administering compounds which directly inhibit platelet aggregation.

SUMMARY OF THE INVENTION

One object of this invention is to provide a method for inhibiting platelet aggregation. A feature of this invention is a method for inhibiting platelet aggregation, which comprises administering a compound which mimicks a γ-turn around the Asp residue of the Arg-Gly-Asp peptide sequence.

Another feature of this invention is a compound of the formula (II):

(II)

wherein:
Q is NR' or O;
D is

E and F are (H,H), O or S;
G is N or C;
V is H, R', SR', A-B-O, or A-B-NR';
A is H, R', (CH$_2$)$_n$Ar, R$_1$CO, R$_1$OCO, R$_1$OCH(R$_1$,)CO, R$_1$NHCH(R$_1$,)CO, R$_1$SCH(R$_1$,)CO, R$_1$SO$_2$ or R$_1$SO;
R$_1$ and R$_1$, are H, C$_{1-5}$alkyl, C$_{3-7}$cycloalkyl, aryl or aryl substituted by one or two C$_{1-5}$alkyl, trifluoromethyl, hydroxy, C$_{1-5}$alkoxy or halogen groups;
R$^2$ is N(R')$_2$, NR'C(=O)NHR', C(=NR')NHR' or NR'C(=NR')NHR';
B is absent, Arg, HArg, (Me$_2$)Arg, (Et$_2$)Arg, Ala, Gly, His, Abu or an α-R' substituted derivative thereof, or Pro;
X is R", CHRCH$_2$-Y-Z or CHRCO-Y-Z;
Y is absent or a D- or L- amino acid chosen from Tyr, (Alk)Tyr, Phe, (4'W)Phe, HPhe, Phg, Trp, His, Ser, (Alk)Ser, Thr, (Alk)Thr, Cys, (Alk)Cys, Pen, (Alk)Pen, Ala, Val, Nva, Met, Leu, Ile, Nle and Nal;
Z is R" or OR", NR'R" or R";
R is H, C$_{1-6}$alkyl, (CH$_2$)$_n$Het, (CH$_2$)$_n$CONHR', (CH$_2$)$_n$NR'R', (CH$_2$)$_n$NC=N-NR', (CH$_2$)$_n$OR' or (CH$_2$)$_n$SR' or (CH$_2$)$_n$Ar;
R' is H, C$_{1-4}$ alkyl or (CH$_2$)$_n$Ar;
R" is H, C$_{1-6}$alkyl, C$_{3-7}$cycloalkyl, amino, Ar, (CHR')$_n$(CH$_2$)$_n$-Ar, C$_{3-7}$cycloalkyl-Ar, Het, (CH$_2$)$_n$Het or C$_{3-7}$cycloalkyl-Het;
Ar is phenyl or naphthyl optionally substituted by one or two C$_{1-6}$alkyl, C$_{1-6}$alkoxy, C$_{1-6}$alkylthio, CO$_2$R', CON(R')$_2$, hydroxy, halogen, trifluoromethyl, amino or nitro groups.
Het is pyridyl, indolyl, imidazolyl or thienyl substituted by one or two C$_{1-4}$alkyl, CO$_2$R', CON(R')$_2$, OR' or SR';
-- is a single or double bond;
m is 0 to 2;
n is 0 to 3;
p is 1 to 3;
q is 1 to 4; and
pharmaceutically acceptable salts thereof.

In another aspect, this invention is a pharmaceutical composition comprising a compound of formula (II) and a pharmaceutically acceptable carrier. The method of inhibiting platelet aggregation comprises administering an effective amount of a compound of formula (II).

Another object of this invention is to provide a method for effecting thrombolysis and inhibiting reocclusion of an artery or vein in a mammal. The method comprises internally administering to a mammal in need thereof, an effective amount of a fibrinolytic agent and a compound of formula (II).

A feature of this invention is a pharmaceutical composition comprising a fibrinolytic agent and a compound of formula (I). Yet another feature of this invention is a kit which comprises, in separate containers, a fibrinolytic agent and a compound of formula (II).

DETAILED DESCRIPTION OF THE INVENTION

This invention discloses a method for producing compounds which inhibit platelet aggregation, which comprises preparing a compound which mimics a γ-turn, around the Asp residue of the Arg-Gly-Asp peptide sequence. Such turns are also commonly referred to as C7 turns, and the compounds may also be referred to as C7 mimics. The compounds of this invention inhibit platelet aggregation and are believed to interact with the GPIIb-IIIa receptor and other adhesion proteins.

A γ-turn conformation around a particular residue (i+1) of a peptide can be defined as a conformation which allows the carbonyl of the i th amino acid residue of a peptide chain to hydrogen bond to the hydrogen attached to the α-nitrogen of the i+2 amino acid residue of the same peptide chain as depicted in formula (III). With reference to (III)

(IV)

Arg-Gly-Asp, it is contemplated that the Gly and Asp residues are involved in a C7 turn. Accordingly, within formula (III), $R_2$ is viewed as representing the sidechain of Gly and $R_3$ represents the sidechain of Asp.

A γ-turn conformation may also xbe defined as the conformation which results when the torsion angles of the i+1 residue are limited to the approximate range of $\Phi i+1$ 70° to 85°= or −70° to −85° and $\psi i+1$= −60° to −70° or 60° to 70°.

According to this invention the hydrogen bond depicted in formula (III) is replaced by a covalent bond to arrive at a γ-turn mimic. Thus, compounds which form a 7-membered cyclic structure as depicted in formula (IV), wherein any member of the ring may be a heteroatom (e.g. N, O, S) or a carbon, provided that such substitution results in a stable chemical structure, are considered γ-turn mimics according to this invention.

Generally, with reference to formula (IV), substituents in the 1-position of the ring are considered to mimic amino acids to the carboxy terminus of the C7 turn and substituents in the 5-position are considered to mimic amino acids to the amino terminus of the C7 turn. Substituents in the 3-position are considered to mimic the side chain of the i+1 th amino acid. Unsaturation may be introduced into the C7 ring to confer additional conformational constraint. Unsaturation is particularly appropriate in the Δ-4,5 and Δ-5,6 positions for mimicking the planar amide moiety, when the 4, 5 and 6 positions are carbon atoms. A preferred functional group for the substituent in the 3-position is a carboxyl group. A preferred functional group for the substituent in the 5-position is a derivatized amino or guanidino group. Accordingly, in one embodiment, this invention is a method for inhibiting platelet aggregation in a mammal which comprises administering a compound having the partial structure (IV):

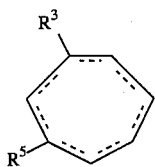

(IV)

wherein $--$ indicates a single or double bond, provided that 2 double bonds are not adjacent within the ring, $R^5$ is a substituent which contains a derivatized amino or guanidino group less than 10 and greater than 6 covalent bonds from the ring, $R^3$ is a substituent which contains a carboxyl group less than 3 covalent bonds from the ring, and the ring optionally contains one or more heteroatoms and substituents which result in a stable structure, such that the compound has about the same or a lower $IC_{50}$ in vitro for platelet aggregation than Ac-Arg-Gly-Asp-$NH_2$, as hereinafter described. Covalent bonds may occur as between a carbon atom and a sulfur, nitrogen, oxygen or another carbon atom as result in a stable chemical structure. It will be understood that the C7 ring may be optionally substituted in the 1, 2, 4, 6 or 7 positions. For instance, the 2 or 4 positions may be substituted by =O. It will be further understood that a heteroatom, such as oxygen, sulfur or nitrogen, may be at any position in the ring, and the ring may contain single or double bonds, as result in stable chemical structure and are available by common methods of organic synthesis.

In one embodiment the heteroatom is a nitrogen in the 1 position, and the compound has the partial structure (V):

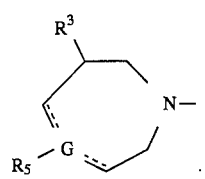

(V)

In a more particular embodiment, this invention is a compound of formula (II):

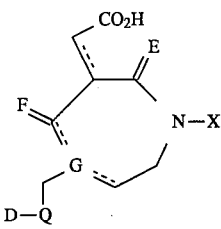

(II)

wherein D, E, F, G, Q and X are as described previously for formula (II), and $--$ is a single or double bond. In yet more specific embodiments, this invention is a compound of formula (VI) or (VII), wherein D, E, F, Q and X are as defined for

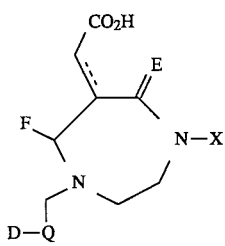

(VI)

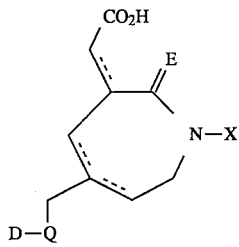

(VII)

formula (II).

Suitably Q is NH.

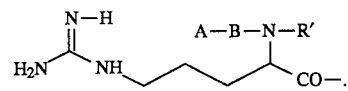

Suitably D is
Suitably A is benzoyl.
Suitably B is absent.
Suitably Y is absent.
Suitably Z is phenyl.
Preferably E is O.

The compounds described herein may have one or more chiral centers. It will be understood that this invention includes each unique nonracemic compound which may be synthesized and resolved by conventional techniques, as well as racemic or diasteromeric mixtures thereof. It will also be evident to those skilled in the art that $--$ does not represent two cumulative double bonds within the cycloheptyl ring; and that when G is N, -- represents a single bond to N; and that when F is =O or =S, -- represents a single bond to the carbon bearing the F substituent, in formula (II).

Het represents a known substituted or unsubstituted heterocycle containing one or two heteroatoms. Representative heterocycles are pyridyl, indolyl, imidazolyl, furyl and thienyl. The heterocycle may be optionally substituted by one or two $C_{1-4}$alkyl, $CO_2R'$, $CON(R')_2$, $OR'$ or $SR'$, wherein R' is defined as for formula (II). Heteroatoms as used herein refer to nitrogen, oxygen and sulfur.

Ar is phenyl or naphthyl optionally substituted by one or two $C_{1-5}$alkyl, $C_{1-5}$alkoxy, $C_{1-5}$alkylthio, $CO_2R'$, $CON(R')_2$, hydroxy, halogen, trifluoromethyl, amino or nitro groups.

Specific compounds of this invention are:

1-phenyl-2-oxo-3-carboxymethyl-5-[benzoyl-(N-methylarginyl)-aminomethyl] -2,3,6,7-tetrahydro-1H-azepine, and 1-phenyl-2-oxo-3-carboxymethyl-5-[acetyl-(N-methylarginyl-aminomethyl] -2,3,6,7-tetrahydro-1H-azepine.

The nomenclature commonly used in the art is used herein to describe the peptides.

| Amino Acid | 3 letter code |
|---|---|
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Glycine | Gly |
| Histidine | His |
| Isoleucine | Ile |
| Asparagine or Aspartic Acid | Asx |
| Glutamine or Glutamic Acid | Glx |
| Leucine | Leu |
| Lysine | Lys |
| Methionine | Let |
| Phenylalanine | Phe |
| Proline | Pro |
| Serine | Ser |
| Threonine | Thr |
| Tryptophan | Trp |
| Tyrosine | Tyr |
| Valine | Val |

In accordance with conventional representation, the amino terminus is on the left and the carboxy terminus is on the right. Unless specified otherwise, all chiral amino acids (AA) are assumed to be of the L-absolute configuration. HArg refers to homoarginine, $(Me_2)Arg$ refers to N', N"-dimethyl arginine, $(Et_2)Arg$ refers to N', N"-diethyl arginine, Nva refers to norvaline, Nle refers to norleucine, Nal refers to beta-2-naphthyl alanine, Phg refers to phenylglycine, HPhe refers to homophenylalanine, Abu refers to 2-amino butyric acid, (Alk)Tyr refers to O-$C_{1-4}$alkyl-tyrosine, (Alk)Ser refers to O-$C_{1-4}$alkyl-serine, (Alk)Thr refers to O-$C_{1-4}$ alkylthreonine, (Alk)Cys refers to S-$C_{1-4}$alkyl-cysteine, (Alk)Pen refers to S-$C_{1-4}$alkyl-penicillamine, (4'W)Phe refers to phenylalanine substituted in the 4 position of the phenyl ring by W, t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the carbobenzyloxy radical, BrZ refers to the o-bromobenzyloxycarbonyl radical, ClZ refers to the o-chlorobenzyloxycarbonyl radical, Bzl refers to the benzyl radical, 4-MBzl refers to the 4-methylbenzyl radical, Ac refers to acetyl, Alk refers to $C_{1-4}$ alkyl, Ph refers to phenyl, Nph refers to 1- or 2-naphthyl, cHex refers to cyclohexyl, BOP refers to benzotriazol-1-yloxytris(dimethylamino)phosphonium hexafluorophosphate, DCC refers to 1,3-dicyclohexylcarbodiimide, DEAD refers to diethyl azo-dicarboxylate, DMAP refers to 4-dimethylaminopyridine, DIEA refers to diisopropylethyl amine, EDC refers to N-ethyl-N' (dimethylaminopropyl)-carbodiimide, HOBt refers to 1-hydroxybenzotriazole, NMM refers to 4-methylmorpholine, THF refers to tetrahydrofuran, DMF refers to dimethyl formamide, HF refers to hydrofluoric acid and TFA refers to trifluoroacetic acid. $C_{1-4}$alkyl as applied herein is meant to include methyl, ethyl, propyl, isopropyl, butyl, isobutyl, sec-butyl, t-butyl. $C_{1-6}$alkyl includes, additionally, pentyl, isopentyl and hexyl, isohexyl, 3-methylpentyl, 2-methylpentyl, 1-methylpentyl, 2-ethylbutyl, and 1-ethylbutyl.

$\alpha$-R' substituted derivatives of the amino acids of this invention, which may be denoted as $(\alpha$-R')AA, indicate amino acids which are mono-substituted on the $\alpha$-amino group by R', wherein R' is, for instance, Alk or benzyl. $N^\alpha$-methyl arginine and $N^\alpha$-methyl glycine, which are $(\alpha$-Me)Arg and $(\alpha$-Me)Gly respectively, are also denoted herein as MeArg and Sar (sarcosine) in accordance with past conventional notation.

Compounds of this invention of the general formula (II):

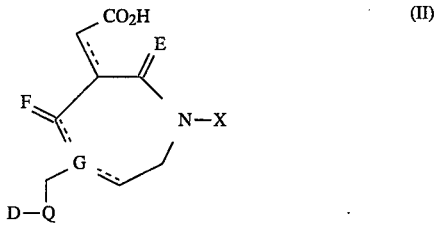

wherein D, E, Q and X are as defined previously for formula (II), are prepared by reacting a compound of the formula (VI):

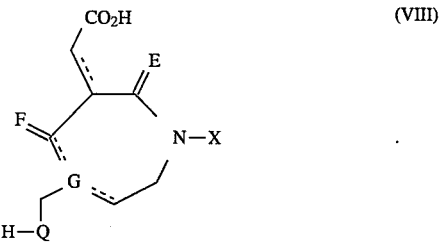

wherein X is as defined for formula (II) with any reactive groups protected; Q and E are as defined for formula (II); and $R_p$ is a carboxyl protecting group; i.) with a carboxylic acid of the formula D-OH, wherein D is defined as in formula (II) with any reactive groups protected, and a coupling reagent, and, thereafter, ii.) removing any protecting groups.

The coupling may be effected by any single or multistep method common to the art. Typically the carboxylic acid and (VIII) are stirred in a solution of a suitable solvent, such as DMF, and a suitable carbodiimide reagent is added, such as DCC, EDC or BOP. Catalysts, such as HOBt, DMAP or NMM may also be added.

Other methods, such as the formation of activated esters, anhydrides or acid halides of the carboxylic acid, and subsequent reaction with (VIII), optionally in the presence of a base, are also suitable methods of coupling. Typical reagents used for such couplings are thionyl chloride, oxalyl chloride and isobutyl chloroformate. For example, D-OH is treated in an anhydrous solvent, such as methylene chloride or tetrahydrofuran(THF), in the presence of a base, such as 4-methylmorpholine, DMAP or a trialkylamine, with isobutyl chloroformate to form the "activated mixed anhydride", which is subsequently reacted with the amino or hydroxyl group (H-Q is OH, NHR').

If desired, the amino acid residues B and D may be added sequentially, using common methods of peptides synthesis. Typically, a protected Boc-amino acid which has a free carboxyl group is coupled to the free amino or hydroxyl group (H-Q) using a suitable carbodiimide coupling agent, such as DCC, in the presence of HOBt or DMAP. Removal of the Boc group with acid, and repetition of the coupling cycle with a second Boc-amino acid provides a sequential coupling of the two amino acids. Subsequent removal of the Boc group with acid, and further acylation, sulfonylation or alkylation completes the sequence.

As is common in the chemical and peptide arts, reactive functionalities which may be incompatible with certain reaction conditions are often protected during the synthesis. Reactive groups which may be optionally protected include carboxylic or sulfonic acid, hydroxyl, amino, thio, guanidino and imidazole functionalities. Common methods for protection and deprotection of these moieties is described in Greene et al., "Protective Groups in Organic Synthesis", John Wiley and Sons, New York (1991). Acids are normally protected by forming aryl, aralkyl or aliphatic esters, such as $C_{1-6}$alkyl, phenyl, naphthyl or benzyl esters, and are deprotected by normal methods of hydrolysis or hydrogenation. Methyl, cyclohexyl and benzyl esters are particularly useful. The hydroxyl group is commonly protected as an ether, particularly a silyl ether, or an ester. Tetrahydropyranyl-, trimethylsilyl, t-butyldiphenylsilyl ethers and t-butyldimethylsilyl-ethers, and acetyl- and benzoyl-esters are representative protecting groups for the hydroxyl moiety. The Boc, Cbz or Fmoc group may be used for protection of an amino group. A benzyl group or suitably substituted benzyl group is used to protect the mercapto group. Alternatively, a mercapto group may be protected as a disulfide, such as with ethyl sulfide The imidazole group is commonly protected by a Boc or trimethylsilylethoxymethyl (SEM) group. The tosyl or nitro group may be used for protection of the guanidino group. Except for the Boc group, the protective groups are, most conveniently, those which are not removed by mild acid treatment. These protective groups are removed by such methods as catalytic hydrogenation, fluoride ion, sodium in liquid ammonia or HF treatment as known in the art.

Compounds of formula (II) wherein Q is NR' and G is C, are formed according to the method of Scheme 1. Generally, a Birch Scheme 1

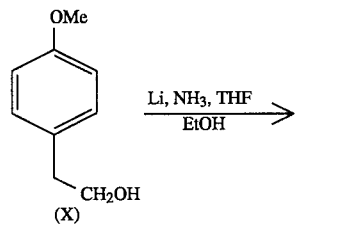

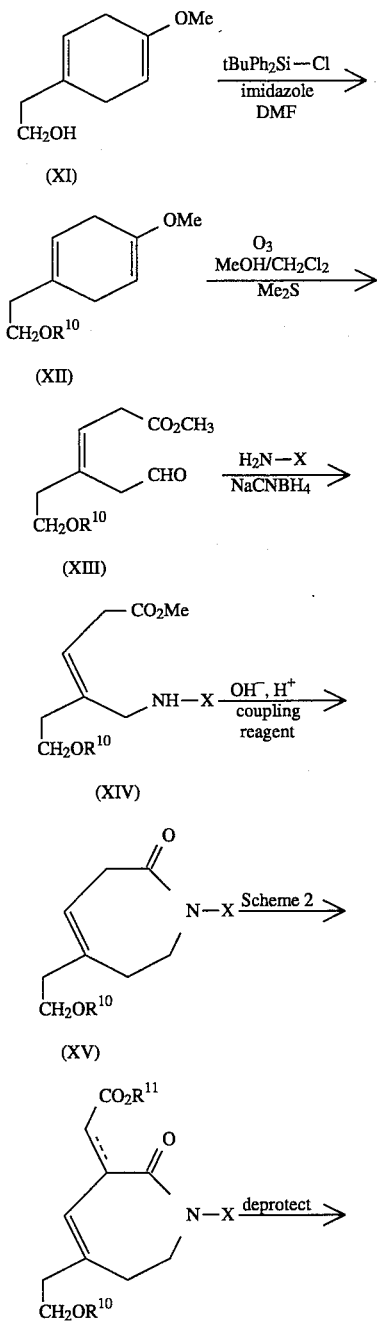

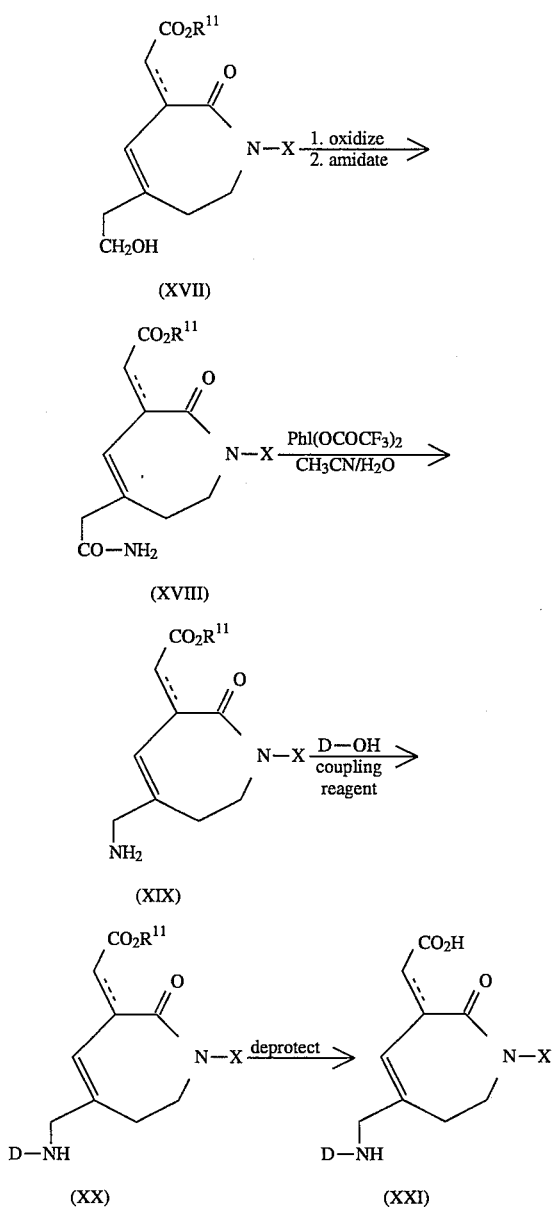

reduction upon 2-(p-methoxyphenyl)ethyl alcohol (X) with lithium and liquid ammonia yields the corresponding 4-(2-hydroxy)ethyl- 1-methoxy-cyclohexa-1,4-diene (XI). Protection of the hydroxyl group is accomplished with an appropriate protective group, such as a silyl ether, for instance a t-butyldiphenyl silyl ether. Selective ozonolysis of the diene and standard workup with dimethylsulfide yields the corresponding methyl 6-oxo-4-(2-(silyl ether protected-hydroxy)ethyl)-hex- 3-enoate (XIII).

Reductive amination of the 6-aldehyde function with an appropriately protected amine, such as $H_2N$-X, yields a compound of the formula (XIV), as shown in scheme 1, wherein X is as defined for formula (II) with any reactive groups protected. As will be appreciated by those skilled in the art, when convenient or appropriate, for example when $H_2$N-X is $H_2$N-$CHRCH_2$-Y-Z or $H_2$N-CHRCO-Y-Z, it is possible to reductively aminate only with an appropriately protected fragment of the X group, such as $H_2$N-CHRCO-$R_p$. The remaining Y and/or Z group, as described in formula (II), are then coupled or added to the fragment later in the synthesis using conventional methods. Reductive amination is accomplished by stirring the amine and the aldehyde in an appropriate solvent, such as an aliphatic alcohol, and treating the solution with a mild reducing agent, such as sodium or lithium cyanoborohydride.

The azepine ring structure (XV) is formed by hydrolyzing the ester function in the 1-position using an appropriate base, such as an alkali metal hydroxide, reacidifying to obtain the carboxylic acid, and treating the resulting amino acid with a coupling reagent. Carbodiimide coupling reagents, such as DCC and EDC, optionally with catalysts such as HOBt, DMAP or NMM, or conversion of the acid to an activated acyl group, such as an activated ester or acyl halide, and subsequent treatment with base is suitable. Use of the BOP coupling reagent with HOBt and NMM in DMF solution has been found to be particularly suitable.

Introduction of the substituent in the 3-position of the azepin-2-one, is accomplished by treating the azepinone with a suitable base, such as lithium diisopropylamide or lithium hexamethyldisilazane, and an appropriate alkylating agent as in Scheme 2.

Scheme 2

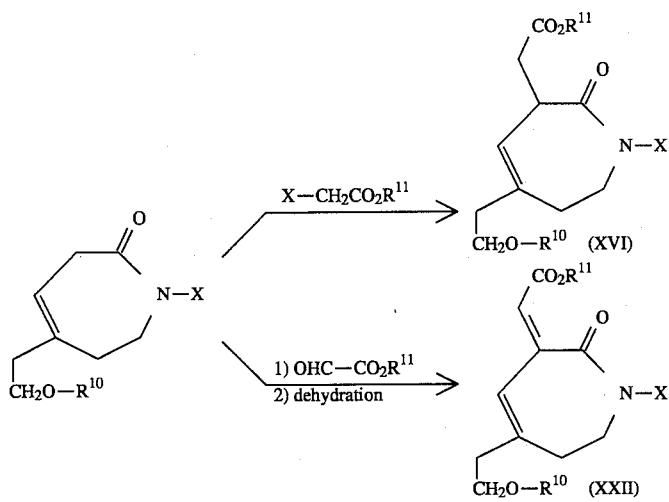

If a carboxymethyl group is desired, as in formula (XVI), in the 3-position of the final product, a protected α-halo acetate is suitable. Benzyl α-iodoacetate is a suitable alkylating agent. If a carboxyalkene is desired, as in formula (XXII) of Scheme 2, then an appropriately protected glyoxaldehyde is used as the alkylating agent. Subsequent treatment of the resulting α-hydroxy-ester, with an acid, such as hydrochloric acid, yields the corresponding carboxyalkene. Alternately, conversion of the hydroxyl group to an appropriate leaving group, such as an acetate, and treatment with a base, such as DBU will also afford the carboxy-alkene at the 3-position.

The substituent at the 5-position is added by coupling to an alcohol or amine functionality. If an aminomethyl function is desired at the 5-position (i.e. Q is NR'), then the alcohol function is deprotected, converted to a carboxamide and rearranged, as in a Curtius-type reaction. If a silyl ether is used as the protecting group, then deprotection is most conveniently accomplished by treating the protected alcohol with a fluoride reagent, such as tetrabutylammonium fluoride or pyridinium fluoride, to afford the free alcohol (XVII). Oxidation of the alcohol with a strong oxidizing reagent, such as Jones reagent, provides the corresponding carboxylic acid. The carboxylic acid may be converted to the acyl azide by conventional means, for instance, by preparing an activated anhydride or acyl halide and treating with sodium azide. Heating the resulting acyl azide, followed by aqueous workup provides the corresponding aminomethyl substituent at the 5-position. Alternately, the carboxylic acid may be converted to the carboxamide (XVIII), for instance, by preparing an activated anhydride or acyl halide and treating with ammonia. Treatment of the resulting carboxamide with [bis(trifluoroacetoxy)iodo]benzene also yields the corresponding aminomethyl substituent as in formula (XIX).

Coupling of the amine to a carboxylic acid of the formula D-OH (or a dipeptide of the formula A-B-D-OH), using conventional methods for forming peptide bonds as previously described, yields the final protected product (XX). Of course it will be recognized that the residues A, B and D may also be added sequentially, using appropriate protecting groups and common methods of peptide synthesis, as previously described. Removal of all protecting groups, using acid or base hydrolysis, or catalytic hydrogenation yields the final azepin-2-one (XXI). Deprotection using hydrofluoric acid is particularly suitable.

Compounds wherein the 4,5 and 5,6 bonds are single bonds, as in formula (XXIII) are prepared in the same manner

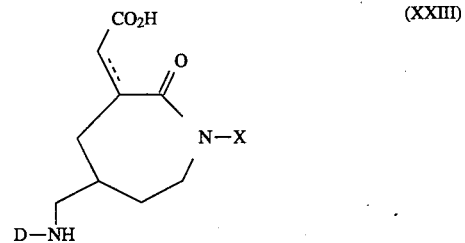

as in Scheme 1, except the double bond of intermediate (XIII) is reduced using hydrogen and 5%–10% palladium on carbon catalyst, as shown in Scheme 3. An unreactive solvent, such Scheme 3

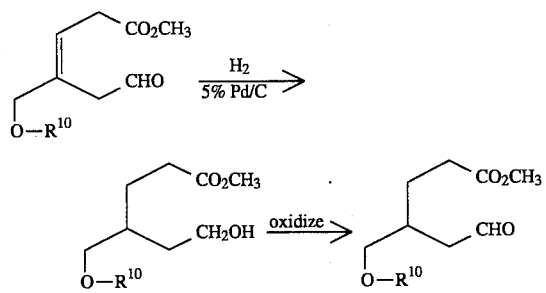

as ethyl acetate or ethanol, is suitable for the reduction. Reoxidation of the aldehyde, using a mild oxidizing reagent, such as pyridinium chlorochromate or oxallyl chloride/ dimethyl sulfoxide/triethylamine in methylene chloride (the Swern method), provides a saturated aldehyde which is suitably carried through the remainder of Scheme 1.

Compounds wherein the 4,5 bond is a single bond and the 5,6 bond is a double bond are prepared according to Scheme 4, employing methodology analogous to Scheme 1. Similar methodology is also disclosed by Huffman et al., Peptides: Chemistry and Biology, Proceedings of the Tenth American Peptide Symposium, Marshall, G. ed., ESCOM, Leiden, 105 (1988), and Huffman et al., Synthetic Peptides: Approaches to Biological Problems., UCLA Symposium on Molecular and Cellular Biology, 86, Tam, J. and Kaiser, T. ed., Alan R. Liss, Inc., New York, 257 (1989). t,201

Accordingly, 4-methoxybenzyl alcohol (XXX) is reduced with lithium in liquid ammonia and quenched with ethanol, in a Birch-type reduction, to afford the (4-methoxy-2,5-cyclohexadienyl)methyl alcohol (XXXI). Protection of the hydroxyl, for instance as a silyl ether, yields the corresponding protected diene (XXXII). Selective ozonolysis of the diene and standard dimethyl sulfide workup yields the methyl 6-oxo-5-(protected-hydroxy)methyl-hex-4-(E)-enoate (XXXIII). Treatment of the β,γ-unsaturated aldehyde (XXXIII) with base, such as triethylamine, DBU or sodium carbonate, in an inert solvent, such as THF, ethyl acetate or methylene chloride, induces an isomerization to yield the α,β-unsaturated aldehyde, methyl 6-oxo-5-(protected-hydroxy)methyl-hex- 5-(E)-enoate (XXXIV). Reductive amination of aldehyde (XXXIV) with $H_2N-X$ to produce amine (XXXV), hydrolysis of the ester, and intramolecular coupling of the acid to the amine yields azepinone (XXXVI). Treatment of the azepinone (XXXVI) with base and an electrophile to produce the 3-substituted azepinone (XXXVII), and deprotection of the hydroxyl function proceed in direct analogy to the procedure in Scheme 1. Reaction of the alcohol (XXXVIII) with triphenylphosphine and diethyl azodicarboxylate and phthalimide in an inert solvent, such as THF, and deprotection of the resulting protected amine with hydrazine hydrate in ethanol produces amine (XXXIX). Coupling of the side chain carboxylic acid D-OH, and removal of the protecting groups, as previously described, yields the Δ-4,5-azepin-2-one (XLI).

Depsipeptides (Q is O) of the general formula (XLII) are prepared by the method of Scheme 4, except omitting the step of reacting the alcohol (XXXVIII) with triphenylphosphine and diethyl azodicarboxylate and phthalimide. t,220

Depsipeptides of the general formula (XLIII) are prepared by the method of Scheme 4, except 1) the step of isomerization of the double bond of aldehyde (XXXIII) is omitted; 2) the alkylation step is modified to introduce an incipient carboxymethyl group, such as an allyl group which is later selectively converted to the desired acid; and 3) the step of reaction of alcohol (XXXVIII) with triphenylphosphine, diethyl azodicarboxylate and phthalimide is omitted.

Depsipeptides of the general formula (XLIV) are prepared by the method of Scheme 4, except 1) the double bond of aldehyde (XXXIII) is reduced, as described in Scheme 3, and 2) the step of reaction of alcohol (XXXVIII) with triphenylphosphine and diethyl azodicarboxylate and phthalimide is omitted.

Compounds of formula (II) wherein E is =S and F is (H,H), are given by formula (XLV), and are

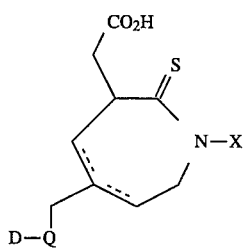

prepared according to Scheme 1 or 4, except the amide (E is =O) in the C7 ring is converted to a thioamide (E is =S) after the alkylation step at position 3. Accordingly, compound (XVI) (Scheme 1) or compound (XXXVII) (Scheme 4) is treated with Lawesson's reagent, (2,4-bis(4-methoxyphenyl)-1,3-dithia- 2,4-diphosphetane-2,4-disulfide), in a dry inert solvent, such as toluene, benzene or tetrahydrofuran, with heating if necessary, to produce the thioamide. The resulting thioamide intermediate is then carried through the remaining steps of the synthetic scheme to prepare compounds of the formula (XLV).

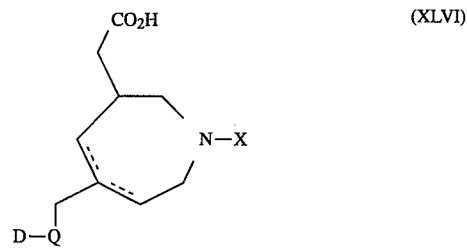

Compounds of formula (II) wherein E is (H,H) and F is (H,H), given by formula (XLVI), are prepared according to Scheme 1 or 4, except the amide carbonyl is reduced to a methylene unit. This is most conveniently accomplished through the intermediacy of the thioamide described above. The thione moiety is reduced by treatment of the thioamide with triethyloxonium tetrafluoroborate under an inert atmosphere in a non-reactive solvent, such as methylene chloride, and subsequent treatment with sodium borohydride and methanol. Standard acid workup provides the azepine ring system, as depicted in Scheme 5, which is then carried.

Scheme 5

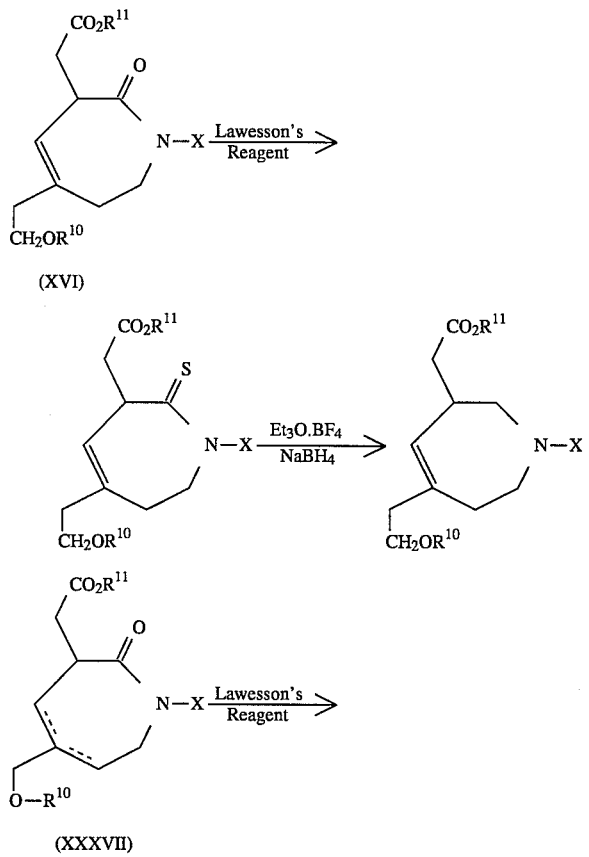

-continued
Scheme 5

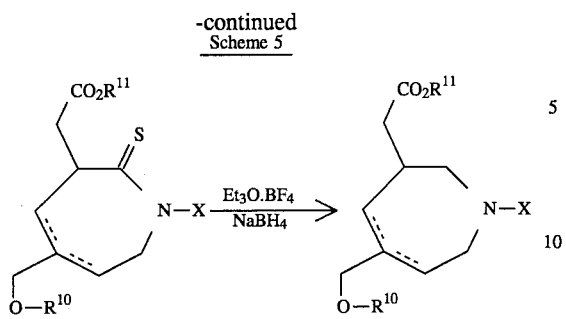

through the remaining steps of the reaction scheme to prepare the compounds of formula (XLVI).

Compounds of formula (II) wherein F is O and G is N, are prepared according to a method analogous to Scheme 6. The ring system is prepared by cyclization of a 6-amino-alkanoic acid. For example, the incipient nitrogen (G=N) may be introduced by alkylating the nitrogen of a protected glycine with an alkyl group substituted by an incipient amino moiety, which can be further acylated with a mono-ester of malonic acid. Deprotection of the amino and carboxyl groups followed by coupling of the resulting amino acid forms the 7-membered ring. Alternately, if an additional amide moiety within the ring is not desired, glycine may be alkylated with an appropriately protected substituted alkanoic acid, which may be further cyclized to the glycine nitrogen. The further introduction of substituents and elaboration of sidechains follows much the same methodology as described in detail in Schemes 1–5.

Scheme 6

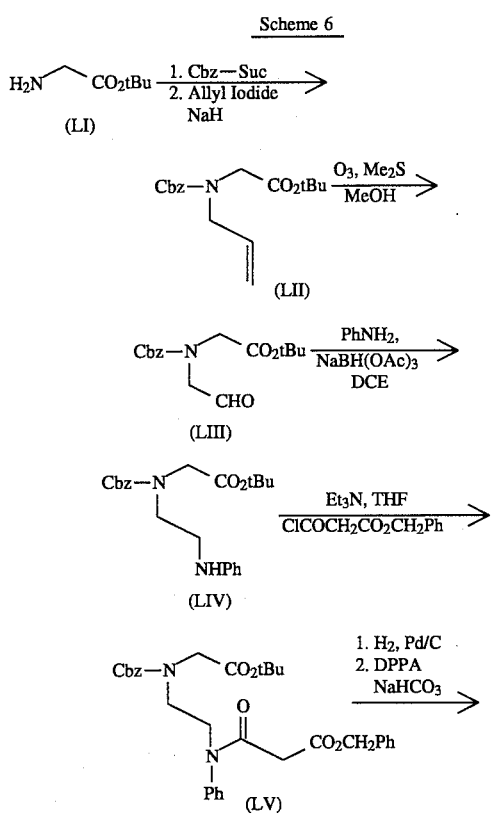

-continued
Scheme 6

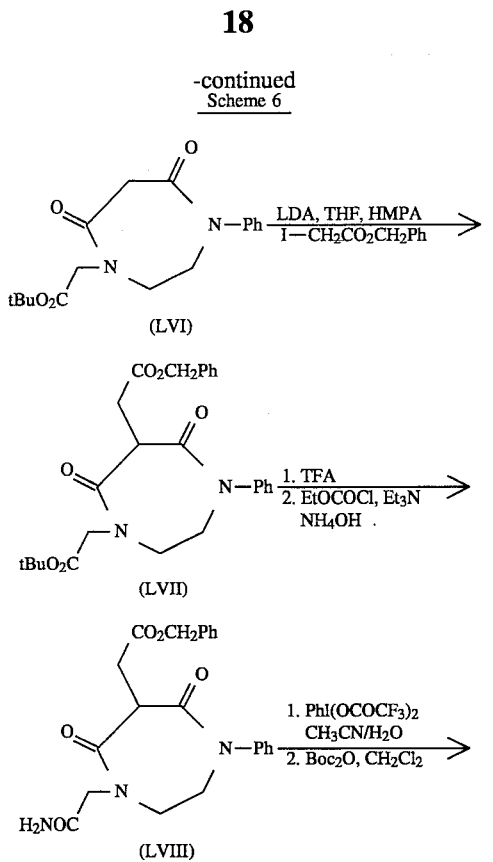

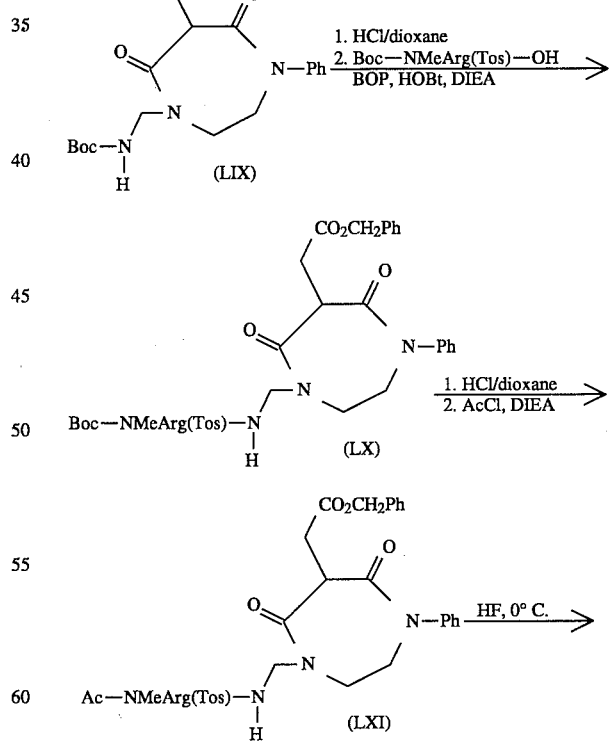

-continued
Scheme 6

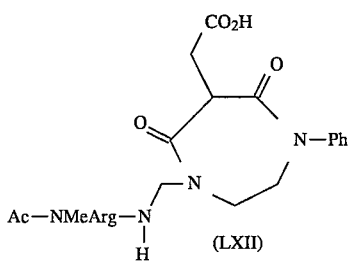

(LXII)

The α-R' substituted derivatives of the amino acids of this invention, which includes derivatives of Arg, HArg, (Me$_2$)Arg, (Et$_2$)Arg, Ala, Gly, His, Abu, Tyr, (Alk)Tyr, Phe, (4'W)Phe, HPhe, Phg, Trp, His, Set, (Alk)Ser, Thr, (Alk)Thr, Cys, (Alk)Cys, Pen, (Alk)Pen, Ala, Val, Nva, Met, Leu, Ile, Nle and Nal, are prepared by methods common to the chemical art. The R' substituent may be Alk, as hereinbefore defined, or benzyl. Representative methods for preparing these derivatives are disclosed in U.S. Pat. No. 4,687,758; Cheung et al., *Can. J. Chem.*, 55, 906 (1977); Freidinger et al., *J. Org. Chem.*, 48, 77, (1982); and Shuman et al., *Peptides: Proceedings of the 7th American Peptide Symposium*, Rich, D., Gross, E., Eds, Pierce Chemical Co., Rockford, Ill., 617 (1981), and EP-A 0 275 748, which are incorporated herein by reference.

Acid addition salts of the peptides are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$, and NH$_4^+$ are specific examples of cations present in pharmaceutically acceptable salts.

This invention provides a pharmaceutical composition which comprises a peptide according to formula (II) and a pharmaceutically acceptable carrier. Pharmaceutical compositions of the compounds of this invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these peptides may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the peptides of this invention may also be combined with excipients such as cocoa butter, glycerin, gelatin or polyethylene glycols and molded into a suppository.

This invention also provides a method of inhibiting platelet aggregation and clot formation in a mammal, especially a human, in need thereof, which comprises the internal administration of a compound according to formula (II) and a pharmaceutically acceptable carrier. Indications for such therapy include myocardial infarction, deep vein thrombosis, pulmonary embolism, dissecting anurysm, transient ischemia attack (TIA), stroke and other infarct-related disorders. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the peptides of this invention may be used in a method for the prevention of metastatic conditions.

The compounds of this invention are administered either orally or parenterally to the patient, in a manner such that the concentration of drug in the plasma is sufficient to inhibit platelet aggregation. The pharmaceutical composition containing the peptide is administered at a dose between about 0.2 to about 50 mg/kg in a manner consistent with the condition of the patient. For acute therapy, parenteral administration is preferred. For persistant states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The peptide is administered one to four times daily at a level of about 0.4 to about 50 mg/kg. to achieve a total daily dose of about 0.4 to about 200 mg/kg/day. No unacceptable toxicological effects are indicated when compounds of this invention are administered in the above noted dosage range.

This invention further provides a method for inhibiting the reocclusion of an artery or vein following fibrinolytic therapy, which comprises internal administration of an effective amount of a compound according to formula (II) and a fibrinolytic agent to a mammal in need thereof. It has been found that administration of an antifibrotic peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents.

Useful plasminogen activators include, for example, anistreplase, urokinase (UK), pro-urokinase (pUK), streptokinase (SK), tissue plasminogen activator (tPA) and routants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334 and in GB 8815135.2. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592 (U.S. Ser. No. 890,432), German Patent Application No. 3032606, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compounds of this invention and fibrinolytic agent in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of this invention is administered just prior to, at the same time as, or just after parenteral administration of tPA or other fibrinolytic agent. It may prove desirable to continue treatment with the compounds of this invention for a period of time well after reperfusion has been established to maximally inhibit post-therapy reocclusion. The effective dose of tPA, SK, UK or pUK may be from 0.1 to 5 mg/kg and the effective dose of the compounds of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials, ampoules or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and anti-fibrotic peptide may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of a compound of this invention followed by an infusion of the fibrinolytic agent.

The pharmacological activity of the peptides was assessed by the following tests:

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629–43 (1980).

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at $3\times10^5$ cells/mL. Peptides were added 3 min. prior to the agonist in all assays of platelet aggregation. Final agonist concentrations were 0.1 unit/mL thrombin and 2 mMADP (Sigma). Aggregation was monitored in a Chrono-Log Lumi-Aggregometer. Light transmittance 5 min after addition of the agonist was used to calculate percent aggregation according to the formula % aggregation =[(90-CR)+ (90-10)]×100, where CR is the chart reading, 90 is the baseline, and 10 is the PRP blank reading. $IC_{50}$'s were determined by plotting [% inhibition of aggregation] vs. [concentration of peptide]. Peptides were assayed at 200 μM and diluted sequentially by a factor of 2 to establish a suitable dose response curve. The $IC_{50}$ of Ac-Arg-Gly-Asp-$NH_2$ in this assay was 91 μM.

To assess the stability of the peptide to plasma proteases, the peptides were incubated for 3 h (rather than 3 min) in the PRP prior to addition of the agonist.

The compounds of Examples 1 and 2 were stable in platelet-rich plasma for up to 3 h and showed an $IC_{50}$ for the aggregation of dog platelets stimulated by ADP of between about 0.5 and 1.5 μM. A preferred compound of this invention is 1-phenyl-2-oxo-3-carboxymethyl-5-[acetyl-(N-methyl-arginylaminomethyl] -2,3,6,7-tetrahydro-1H-azepine.

The examples which follow are intended to in no way limit the scope of this invention, but are provided to illustrate how to make and use the compounds of this invention. Many other embodiments will be readily apparent and available to those skilled in the art.

EXAMPLES

In the examples which follow all temperatures are in degrees Celsius. NMR were performed at 90 MHz with a Varian EM390 spectrometer or at 250 MHz with a Bruker AM250 spectrometer. Chemical shifts are reported in δ units from the internal standard tetramethylsilane. Analtech silica gel GF and EM silica gel thin layer plates were used for thin layer chromatography. Both flash and gravity chromatography were carried out on Merck 60 (230–400 mesh) silica gel. ODS refers to an octadecylsilyl derivatized silica gel chromatographic support. MeArg was prepared by the method disclosed by Ali et al., in U.S. Pat. No. 4,687,758 (1987).

EXAMPLE 1

Preparation of
1-phenyl-2-oxo-3-carboxymethyl-5-[(N-benzoyl-N-methyl-arginylamino)methyl]
-2,3,6,7-tetrahydro-1H-azepine a) 1-Methoxy-4-(2-hydroxyethyl)-cyclohexa-1,4-diene (1).

Liquid ammonia (520 mL) was condensed in a three-necked flask which was fitted with a cold finger and overhead stirrer and kept at −78° C. with a dry ice/isopropanol bath. A solution of 1-methoxy-4-hydroxymethyl-benzene (50 g, 329 mmol) in tetrahydrofuran (140 mL) was added to the reaction flask followed by the addition of small pieces of lithium wire (10.3 g, 1.48 mol) over a period of about 15 min. The reaction mixture was stirred an additional 30 min at −78° C. and then quenched by the slow addition of absolute ethanol (400 mL). After the reaction was completely quenched (white color), it was allowed to warm to room temperature overnight. This allowed most of the $NH_3$ to evaporate. The residue was partitioned between water and diethyl ether, the organic layer collected, dried over anhydrous $MgSO_4$, filtered and evaporated at reduced pressure. The residue, which still contained some water, was dissolved in methylene chloride, dried over anhydrous $MgSO_4$, filtered and evaporated at reduced pressure to give crude 1-methoxy-4-(2-hydroxyethyl)-cyclohexa-1,4-diene (1) as an oil (40.3 g), which was used in the next step without further purification. This crude product was contaminated with the over-reduced product, 1-methoxy-4-(2-hydroxyethyl)-cyclohex- 1-ene (2). Compound (1): $^1$H NMR δ ($CDCl_3$) 2.12 (1H, br s), 2.28 (2H, t, J=7.5 Hz), 2.78 (4H, br s), 3.58 (3H, s), 3.73 (2H, t, J=7.5 Hz), 4.68 (1H, br s), 5.55 (1H, br s).

b) 1-Methoxy-4-[2-(t-butyldiphenylsilyl)hydroxyethyl]-cyclohexa- 1,4-diene (3).

The crude compound (1) was dissolved in N,N-dimethylformamide (150 mL) and treated at room temperature with imidazole (44.8 g, 658 mmol) and t-butyldiphenylsilyl chloride (85.6 mL, 329 mmol). The resulting solution was stirred at room temperature for 2 d (reaction was essentially complete after a few hours) after which time it was diluted with 10% ethyl acetate in hexane, washed 3× with water, dried over anhydrous $MgSO_4$, filtered and evaporated to give crude 1-methoxy-4-[2-(t-butyldiphenylsilyl)hydroxyethyl]-cyclohexa- 1,4-diene (3). The mixture, which was contaminated with the over-reduced product 4-[2-(t-butyldiphenylsilyl)hydroxyethyl] -cyclohex-1-ene (4), was used in the next step without further purification. Compound (3): $^1$H NMR ($CDCl_3$) δ 1.07 (9H, s), 2.25 (2H, t, J=6.0 Hz), 2.70 (4H, s), 3.55 (3H, s), 3.77 (2H, t, J=6.0 Hz), 4.62 (1H, br s), 5.43 (1H, br s), 7.22–7.93 (10H, m).

c) Methyl 4-(ethan-2-oxo)-6-(t-butyldiphenylsilyl)hydroxy-hex- 3-enoate (5).

Crude compound (3) (~164 mmol) from Example 1b was dissolved in a mixture of methanol and dichloromethane (4:1, 500 mL), the resulting solution was cooled to −78° C. and treated with $O_3$ until the diene disappeared by TLC. The reaction mixture was then reduced with methyl sulfide (25 mL) and slowly brought to room temperature where it was stirred for 18 h. The reaction mixture was evaporated at reduced pressure and the residue purified by flash chromatography (silica gel, 10×20 cm column, 15% ethyl acetate/hexane) to yield methyl 4-(ethan-2-oxo)-6-(t-butyldiphenylsilyl)hydroxyhex- 3-(Z)-enoate (5) (26.77 g, 38%), which was contaminated with approximately 31% of the saturated aldehyde, compound (6). Compound (5): $^1$H NMR ($CDCl_3$) δ 1.05 (9H, s), 2.33 (2H, t, J=6.0 Hz), 2.97–3.17 (4H, m), 3.67 (3H, s), 3.73 (2H, t, J=6.0 Hz), 5.77 (1H, t, J=7.5 Hz), 7.27–7.87 (10H, m), 9.63 (1H, t, J=2.4 Hz). Compound (6): $^1$H NMR ($CDCl_3$) δ 1.07 (9H, s), 1.40–2.50 (9H, m), 3.65 (3H, s), 3.72 (2H, t, J=6.0 Hz), 7.27–8.00 (10H, m), 9.80 (1H, t, J=1.5 Hz). Mixture of compounds (5/6): TLC $R_f$ 0.45 (silica gel, 7:3 hexane: ethyl acetate).

d) Methyl 4-(2-phenylamino)ethyl-6-(t-butyldiphenylsilyl)hydroxyhex- 3-enoate (7).

Crude compound (5) (26.77 g, 63 mmol) was dissolved in methanol (400 mL) and treated at 0° C. with aniline (17.2 mL, 189 mmol) and sodium cyanoborohydride (4.35 g, 69.3 mmol) followed by the addition of enough anhydrous HCl in ethanol to lower the pH of the solution to 6. The resulting reaction mixture was stirred at room temperature for 94 h. At this time, the reaction mixture was evaporated at reduced pressure, the residue dissolved in ethyl acetate, washed with water, dried over anhydrous $MgSO_4$, filtered and evaporated at reduced pressure. The residue was purified by flash chromatography (silica gel, 10×20 cm column, 12% ethyl acetate/hexane) to give methyl 4-(2-phenylamino)ethyl-6-(t-butyldiphenylsilyl)hydroxy-hex- 3-(Z)-enoate (7) (22.7 g, 72%), which contained about 31% the saturated side-product methyl 4-(2-phenylamino)ethyl-6-(tbutyldiphenylsilyl)hydroxyhexanoate (8). Mixture of compounds (7/8): $^1$H NMR ($CDCl_3$) δ 1.07 (9H, s), 1.37–3.25 (9.9 H, m), 3.65/ 3.67 (3H, two s), 3.57–4.03 (2H, m), 5.53 (0.7H, t, J=7.5 Hz), 6.50–6.87 (3H, m), 7.07–7.87 (12H, m); TLC $R_f$ 0.64 (silica gel, 7:3 hexane:ethyl acetate).

e) 1-Phenyl-2-oxo-5-[2-(t-butyldiphenylsilylhydroxy)ethyl]- 2,3,6,7-tetrahydro-1H-azepine (9).

Crude compound (7)(21.22 g, 42.3 mmol) was dissolved in dioxane (127 mL) and the resulting solution was treated with 1N NaOH (63.5 mL, aqueous) at room temperature for 4 h. The reaction mixture was then treated with 3N HCl (63.5 mL, aqueous) and evaporated under high vacuum. The residue was re-evaporated from toluene (2×) and the resulting amino acid hydrochloride dissolved in dry N,N-dimethylformamide (1800 mL). The resulting solution was cooled to 0° C. and treated sequentially with 4-methylmorpholine (27.9 mL, 254 mmol), 1-hydroxybenzotriazole (11.4 g, 84.4 mmol) and BOP reagent (37.4 g, 84.6 mmol). The reaction mixture was brought to room temperature and stirred for 3 d. After this time, the reaction mixture was evaporated under high vacuum and the residue purified by flash chromatography to remove polar impurities (silica gel, 8×20 cm column, 75% ethyl acetate/hexane) without achieving any separation of isomers followed by a second flash chromatography (10×20 cm, 30–50% ethyl acetate/hexane) to give three fractions. The first contained 4.34 g (22%) of the title compound (9), the second contained 7.23 g (36%) of a mixture of (9) and the 1-phenyl- 2-oxo-5-[2-(t-butyldiphenylsilylhydroxy)-ethyl]-hexahydro-1H-azepine (10), and the third which contained 751 mg of pure (10). The second fraction was further purified on a gravity column (silica gel, 5×100 cm column, eluted with 25% ethyl acetate in hexane)

to yield an additional 4.6 g of pure (9) (45% overall isolated yield). Compound (9): $^1$H NMR (CDCl$_3$) δ 1.07 (9H, s), 2.12–2.47 (4H, m), 3.33 (2H, br d, J=6.0 Hz), 3.67–4.03 (4H, m), 5.53 (1H, t, J=6.0 Hz), 7.03–8.03 (15H, m); MS (DCI/CH$_4$) m/e 470 (M+H)$^+$; TLC R$_f$ 0.30 (silica gel, 7:3 hexane:ethyl acetate). Compound (10): $^1$H NMR (CDCl$_3$) δ 1.07 (9H, s), 1.30–2.80 (9H, m), 3.57–4.03 (4H, m), 7.07–8.03 (15H, m); TLC R$_f$ 0.24 (silica gel, 7:3 hexane:ethyl acetate).

f) 1-Phenyl-2-oxo-3-(carbobenzyloxy)methyl-5-[2-(t-butyldiphenylsilylhydroxy)ethyl] -2,3,6,7-tetrahydro-1H-azepine (11).

Compound (9) (650 mg, 1.38 mmol) was dissolved in tetrahydrofuran (5 mL) and cooled to −78° C. The resulting reaction mixture was treated with 1.8 mL of a 1M solution of lithium bis (trimethylsilyl)amide in tetrahydrofuran and stirred for 20 min. At this time, benzyl 2-bromoacetate (437 μL, 2.76 mmol) was added, the reaction continued at −78° C. for 10 min and then warmed to room temperature (removed dry ice/isopropanol bath). After the reaction mixture reached room temperature, 10% NH$_4$Cl (aqueous) was added and the resulting mixture was extracted with ethyl acetate. The combined organic fractions were dried over anhydrous MgSO$_4$, filtered and evaporated at reduced pressure. The residue was purified using flash chromatography (silica gel, 4×20 cm, 20– 40% ethyl acetate/hexane) to yield the title compound (11) (388 mg, 46%). Compound (21): $^1$H NMR (CDCl$_3$) δ 1.05 (9H, s), 1.98–2.73 (5H, m), 2.90–3.23 (1H, m), 3.37–3.73 (1H, m), 3.77 (2H, t, J=6.8 Hz), 4.07–4.80 (2H, m), 5.03–5.27 (3H, m), 6.97–7.83 (20H, m); MS (DCI/NH$_4$) m/e 618 (M+H)$^+$; TLC R$_f$ 0.47 (silica gel, 7:3 hexane:ethyl acetate).

g) 1-Phenyl-2-oxo-3-(carbobenzyloxy)methyl-5-[(2-hydroxy)ethyl] -2,3,6,7-tetrahydro-1H-azepine (12).

Compound (11) (388 mg, 0.628 mmol) was dissolved in tetrahydrofuran (3 mL) and treated at room temperature with 1.26 mL of a 1M solution of tetrabutylammonium fluoride in tetrahydrofuran for 4 h. The reaction mixture was then evaporated at reduced pressure and the residue purified by flash chromatography (silica gel, 2.5×20 cm, 65% ethyl acetate/hexane) to yield the title compound (12) (158 mg, 66%). Compound (12): $^1$H NMR (CDCl$_3$) δ 1.77–3.27 (7H, m), 3.40– 3.73 (1H, m), 3.67 (2H, t, J=6 Hz), 4.20–4.77 (2H, m), 5.07– 5.40 (3H, m), 7.07–7.58 (10H, m); TLC R$_f$ 0.33 (silica gel, 1:3 hexane:ethyl acetate).

h) 1-Phenyl-2-oxo-3-(carbobenzyloxy)methyl-5-(carboxymethyl)- 2,3,6,7-tetrahydro-1H-azepine (13).

Compound (12) (158 mg, 0.416 mmol) in acetone (5 mL) was treated with 500 μL Jones reagent at 0° C. for 1 h. The excess Jones reagent was quenched by the addition of isopropyl alcohol, the reaction mixture diluted with chloroform and washed with water. The combined organic extracts were dried over anhydrous MgSO$_4$, filtered and evaporated at reduced pressure. The resulting crude 1-phenyl-2-oxo-3-(carbobenzyloxy)methyl- 5-(carboxymethyl)-2,3,6,7-tetrahydro- 1H-azepine (13) was then evaporated at reduced pressure from toluene to remove any residual traces of water. Compound (13): $^1$H NMR (CDCl$_3$) δ 2.10–3.76 (7H, m), 4.23–4.83 (2H, m), 5.07–5.27 (2H, m), 5.32 (1H, br s), 7.10–7.63 (10H, m), 8.87 (1H, br s); TLC R$_f$ 0.43 (silica gel, 95:4:1 chloroform:methanol:acetic acid).

i) 1-Phenyl-2-oxo-3-(carbobenzyloxy)methyl-5-(carboxamidomethyl)- 2,3,6,7-tetrahydro-1H-azepine (14).

Crude compound (13) from above was dissolved in tetrahydrofuran (7 mL) and the resulting solution was cooled to −20° C. Triethylamine (232 μL, 1.66 mmol) and ethyl chloroformate (159 μL, 1.66 mmol) were added and the reaction mixture was stirred for 30 min. A mixture of conc. NH$_4$OH (600 μL, aqueous) and tetrahydrofuran (7 mL) was added, the reaction continued at −20° C. for 30 min and then was stored in the refrigerator (~4° C.) for 18 h. The reaction mixture was diluted with ethyl acetate and washed with 3N HCl (aqueous). The organic extracts were combined, dried over anhydrous MgSO$_4$, filtered and evaporated at reduced pressure. The residue was purified by flash chromatography (silica gel, 2.5×20 cm, 5% methanol/chloroform) to yield the title compound (14) (91 mg, 56%). Compound (14): $^1$H NMR (CDCl$_3$) δ 1.95–3.23 (6H, m), 3.38–3.72 (1H, m), 4.22–4.73 (2H, m), 5.07–5.23 (2H, m), 5.33 (1H, br s), 5.82 (1H, br s), 6.05 (1H, br s), 7.08–7.57 (10H, m); TLC R$_f$ 0.34 (silica gel, 95:5 chloroform: methanol).

j) 1-Phenyl-2-oxo-3-(carbobenzyloxy)methyl-5-(aminomethyl)- 2,3,6,7-tetrahydro-1H-azepine trifluoroactetate (15).

Compound (14) (91 mg, 0.232 mmol) was dissolved in a mixture of water and acetonitrile (4:1, 5 mL) and was treated with [bis(trifluoroacetoxy)iodo]benzene (120 mg, 0.278 mmol) at room temperature for 4 h. The reaction mixture was then evaporated at reduced pressure and the residue, containing the crude TFA salt of the title compound (15), was evaporated at reduced pressure 3× from toluene in order to remove any traces of water and udes in the next step without further purification.

k) 1-Phenyl-2-oxo-3-(carbobenzyloxy)methyl-5-[ t-butyloxycarbonyl-(N-methyl-tosyl-arginyl)-aminomethyl]- 2,3, 6,7-tetrahydro-1H-azepine (16).

Compound (15) was dissolved in N,N-dimethylformamide (5 mL) and treated in sequence with Boc-N$^α$-MeArg-(Tos)-OH (154 mg, 0.348 mmol), 1-hydroxybenzotriazole (63 mg, 0.464 mmol), 4-methylmorpholine (153 μL, 1.39 mmol) and BOP reagent (205 mg, 0.464 mmol) at room temperature for 18 h. The reaction mixture was evaporated under high vacuum and the residue was purified by flash chromatography two times (1. silica gel, 2.5×20 cm, 5% methanol/chloroform; 2. silica gel, 2.5×20 cm, 3% methanol/chloroform) to yield the title compound (16) (69 mg, 38%) as an inseparable mixture of diastereoisomers. Compound (16): TLC R$_f$ 0.65 (silica gel, 95:5 chloroform:methanol).

l) 1-Phenyl-2-oxo-3-(carbobenzyloxy)methyl-5-[ benzoyl-(N-methyl-tosyl-arginyl)-aminomethyl]-2,3,6,7-tetrahydro-1H-azepine (17)

Compound (16) (69 mg, 0.087 mmol) from above was treated with anhydrous HCl/dioxane (5 mL) at room temperature for 4 h. The reaction mixture was then evaporated at reduced pressure and then re-evaporated at reduced pressure 2× from toluene to remove any excess HCl. The residue was dissolved in N,N-dimethylformamide (5 mL) and treated with triethylamine (24 μL, 0.174 mmol) and benzoyl chloride (20 μL, 0.174 mmol) at room temperature for 18 h. The reaction mixture was then evaporated under high vacuum and the residue was purified by flash chromatography (silica gel, 2.5×20 cm, 2% methanol in chloroform) to yield the title compound (17) (42 mg, 61%) as an inseparable mixture of diastereoisomers. Compound (17): TLC R$_f$ 0.58 (silica gel, 9:1 chloroform: methanol).

m) 1-Phenyl-2-oxo-3-carboxymethyl-5-[benzoyl-(N-methylarginyl)aminomethyl] -2,3,6,7-tetrahydro-1H-azepine (18).

Compound (17) (42 mg, 0.053 mmol) was dissolved in dichloromethane, transferred to a HF vessel and the solvent evaporated under a stream of argon. Anhydrous HF (10 mL)

was condensed into the vessel at −78° C. and the reaction mixture stirred for 1 h at 0° C. The HF was evaporated at reduced pressure and the residue taken into 10% acetic acid (aqueous) and lyophilized. The resulting powder was dissolved into 50% acetonitrile (aqueous) and purified by repeated runs on a semi-preparative reverse phase hplc column (5μ ODS: IBM, 10×250 mm, flow=4.0 mL/min, 6×500 μL injections) to give, after evaporation and lyophilization from 1% acetic acid (aqueous), 27.5 mg purified the title compound (18) as an inseparable mixture of two diastereomers. Compound (18): MS(FAB) m/e 549 [M+H]$^+$; HPLC k' 2.74 (5μ Apex-ODS: Jones Chromatography, 70:30 water:acetonitrile-0.1% trifluoroacetic acid, UV detection at 220 nm); HPLC k' 5.20 (5μ Apex-ODS, gradient, A: water-0.1% trifluoroacetic acid, B: acetonitrile- 0.1% trifluoroacetic acid, 80-50% during 20 min, UV detection at 220 nm); TLC R$_f$ 0.27 (silica gel, 4:1:1 butanol:acetic acid:water); TLC R$_f$ 0.60 (silica gel, 1:1:1:1 butanol:acetic acid:water:ethyl acetate).

EXAMPLE 2

Preparation of 1-phenyl-2-oxo-3-carboxymethyl-5-[acetyl-(N-methylarginyl)-aminomethyl] -2,3,6,7-tetrahydro-1H-azepine a) 1-Phenyl-2-oxo-3-(carbobenzyloxy)methyl-5-[acetyl-(N-methyl-tosyl-arginyl)aminomethyl] -2,3,6,7-tetrahydro-1H-azepine (19).

Compound (16) (142 mg, 0.180 mmol) from above was treated with anhydrous HCl/dioxane (5 mL) at room temperature for 2 h. The reaction mixture was then evaporated at reduced pressure and then re-evaporated at reduced pressure 2× from toluene to remove any excess HCl. The residue was dissolved in N,N-dimethylformamide (5 mL) and treated with triethylamine (50 μL, 0.360 mmol) and acetyl chloride (26 μL, 0.360 mmol) at room temperature for 18 h. The reaction mixture was then evaporated under high vacuum and the residue was purified by flash chromatography (silica gel, 2.5×20 cm, 2–10% methanol in chloroform) to give 63.2 mg (48%) of the title compound (19) as an inseparable mixture of diastereoisomers. Compound (19): TLC R$_f$ 0.51 (silica gel, 9:1 chloroform: methanol).

b) 1-Phenyl-2-oxo-3-carboxymethyl-5-[acetyl-(N-methyl-tosylarginylamino)methyl] -2,3,6,7-tetrahydro-1H-azepine (20).

Compound (19) (63.2 mg, 0.086 mmol) from above was dissolved in dichloromethane, transferred to a HF vessel and the solvent evaporated under a stream of argon. Anhydrous HF (10 mL) was condensed into the vessel at −78° C. and the reaction mixture stirred for 1 h at 0° C. The HF was evaporated at reduced pressure and the residue taken into 10% acetic acid (aqueous) and lyophilized. The resulting powder was dissolved into 25% acetonitrile (aqueous) and purified by repeated runs on a semi-preparative reverse phase hplc column (5μ ODS, 10×250 mm) to give, after evaporation and lyophilization from 1% acetic acid (aqueous), purified title compound (20) (28.9 mg). Compound (20): MS(FAB) m/e 487 M+H]$^+$; HPLC k' 2.53 (5μ Apex-ODS, 80:20 water:acetonitrile- 0.1% trifluoroacetic acid, UV detection at 220 nm); HPLC k' 1.90 [5μ Apex-ODS, UV detection at 220 nm, gradient, A:water- 0.1% trifluoroacetic acid, B: acetonitrile-0.1% trifluoroacetic acid, 80-50% during 20 min]; TLC R$_f$ 0.16 (silica gel, 4:1:1 butanol:acetic acid:water); TLC R$_f$ 0.46 (silica gel, 1:1:1:1 butanol:acetic acid:water:ethyl acetate).

EXAMPLE 3

Preparation of 1-Phenyl-2,4-dioxo-3-carboxymethyl-5-[(N-acetyl-N-methyl-arginyl)-aminomethyl]-hexahydro-1,5-diazepine (31).

a) N-Allyl-N-benzyloxycarbonyl-glycine t-butyl ester (21b).

A solution of glycine t-butyl ester (15 g, 114 mmol) in methylene chloride 250 mL) was cooled to 0° C. and treated with N-(benzlyoxycarbonyloxy) succinimide (35 g, 137 mmol) at room temperature for 5 h. The reaction mixture was washed with 1N HCl (aqueous), 5% NaHCO$_3$ (aqueous) dried over MgSO$_4$ and evaporated at reduced pressure. The residue was purified by flash chromatography (silica gel, 30% ethyl acetate/hexane) to give benzyloxycarbonyl-glycine t-butyl ester (27.27 g, 90%) (21a). Compound (21a): $^1$H NMR (CDCl$_3$) δ 1.45 (s, 9H), 3.70– 3.95 (m, 2H), 5.12 (s, 2H), 5.43 (br s, 1H), 7.33 (s, 5H).

A solution of compound (21a) (27.27 g, 103 mmol) in anhydrous tetrahydrofuran (200 mL) was treated with allyl iodide (37.6 mL, 411 mmol) and cooled to 0° C. Sodium hydride (60% in oil, 6.15 g, 154 mmol) was added slowly to the reaction mixture and the resulting suspension was stirred at room temperature for 24 h. The reaction mixture was evaporated at reduced pressure and ethyl acetate carefully added to the residue. This solution was washed with saturated Na$_2$S$_2$O$_3$ (aqueous) and water, dried over MgSO$_4$, filtered and evaporated at reduced pressure. The residue was purified by flash chromatography (silica gel, 5–10% ethyl acetate/hexane) to give the title compound (21b) (18.51 g, 60%). $^1$H NMR spectroscopy indicates an interconverting mixture of carbamates (cis/trans). Compound (21b): $^1$H NMR (CDCl$_3$) δ 1.40/1.43 (2s, 9H), 3.70–4.10 (m, 4H), 4.90–5.37 (m, 4H), 5.53–6.17 (m, 1H), 7.32 (s, 5H).

b) N-[1-(Ethan-2-al)]-N-benzyloxycarbonyl-glycine t-butyl ester (22).

A solution of compound (21b) (18.51 g, 60.8 mmol) in methanol (100 mL) was treated with O$_3$ at −78° C. for approximately 1.25 h (until the solution was blue-excess O$_3$). The excess O$_3$ was purge with argon and methyl sulfide was added and the resulting solution was slowly warmed to room temperature and stirred for 24 h. The reaction mixture was evaporated at reduced pressure and the residue was purified by flash chromatography (silica gel, 35% ethyl acetate/hexane) to give the title compound (22) (15.1 g, 81%). $^1$H NMR spectroscopy indicates an interconverting mixture of carbamates (cis/trans). Compound (22): $^1$H NMR (CDCl$_3$) δ 1.40/1.45 (2s, 9H), 3.87–4.20 (m, 4H), 5.15 (br s, 2H), 7.33 (s, 5H), 9.65 (br s, 1H).

c) N-[1-(2-Phenylaminoethyl)]-N-benzyloxycarbonyl-glycine t-butyl ester (23).

A solution of N-[1-(ethan-2-al)]-N-benzyloxycarbonylglycine t-butyl ester (22) (13.2 g, 42.9 mmol) and aniline (4.31 mL, 47.3 mmol) in dichloroethane (200 mL) was cooled to 0° C. and treated sequentially with sodium triacetoxyborohydride (13.6 g, 64.5 mmol) and acetic acid (2.45 mL) and the resulting mixture was stirred at room temperature for 24 h. The reaction was diluted with chloroform, washed 2× with 5% NaHCO$_3$ (aqueous), dried over anhydrous MgSO$_4$, filtered and evaporated at reduced pressure. The residue was purified by flash chromatography (silica gel, 15% ethyl acetate/hexane) to give the title compound (23) (12.47 g, 76%). $^1$H NMR spectroscopy indicates an interconverting mixture of carbamates (cis/trans). Compound (23): $^1$H NMR (CDCl$_3$) δ 1.37/1.45 (2s, 9H), 3.13–3.67 (m, 4H), 3.77–3.95 (m, 2H), 4.25 (br s, 1H), 5.12 (s, 2H), 6.33–6.83 (m, 3H), 6.97–7.27 (m, 2H), 7.30 (s, 5H); MS (FAB) m/e 385 (M+H)$^+$.

d) N-[1-(2-Phenyl-(N-benzylmalonyl)-aminoethyl)]-N-benzyloxycarbonyl-glycine t-butyl ester (24).

A solution of 2,2-dimethyl-1,3-dioxane-4,6-dione (25 g, 174 mmol) and benzyl alcohol (36 mL, 347 mmol) in toluene (100 mL) was heated at 106° C. for 24 h. The solution was poured into 5% Na$_2$CO$_3$ (aqueous), the organic layer was separated, and the aqueous layer was washed with ether (3×). The aqueous layer was then acidified with 1N HCl and extracted with ethyl acetate (2×). The combined ethyl acetate extracts were dried over anhydrous MgSO$_4$, filtered and evaporated at reduced pressure to give malonic acid monobenzyl ester (11.42 g, 34%).

The malonic acid monobenzyl ester (11.42 g, 60 mmol) was dissolved in toluene and treated with excess oxalyl chloride (15 mL) at 35° C. for 24 h. Evaporation of the solvent, along with the excess oxalyl chloride, gave the acid chloride of malonic acid monobenzyl ester (11.4 g).

A solution of compound (23) (1.9 g, 4.97 mmol) in chloroform was treated with pyridine (1 mL) and the acid chloride of malonic acid monobenzyl ester (2.13 g, 10 mmol) and stirred at room temperature for 24 h. The reaction mixture was evaporated at reduced pressure and the residue was dissolved in ethyl acetate, washed with 5% NaHCO$_3$ (aqueous) (2×), 1N HCl (2×) and saturated NaCl (aqueous), dried over anhydrous MgSO$_4$, filtered and evaporated at reduced pressure. The residue was purified by flash chromatography (silica gel, 20–25% ethyl acetate/hexane) to give the title compound (24) (1.86 g, 67%). $^1$H NMR spectroscopy indicates an interconverting mixture of carbamates (cis/trans). Compound (24): $^1$H NMR (CDCl$_3$) δ 1.38/1.43' (2s, 9H), 3.18 (s, 2H), 3.33– 4.00 (m, 6H), 5.00–5.13 (m, 4H), 6.90–7.43 (m, 15H); MS (DCI/NH$_3$) m/e 561 (M+H)$^+$.

e) 1-Phenyl-2,4-dioxo-5-[carbo(t-butyloxy)]methyl-hexahydro-1,5-diazepine (25).

A solution of compound (24) and 5% Pd/C (220 mg) in methanol was treated with H$_2$ at 50 psi (Parr apparatus) at room temperature for 4 h. The reaction mixture was filtered through Celite® to remove the catalysis and then evaporated at reduced pressure. The residue was dissolved in N,N-dimethylformamide (300 mL) and the resulting solution was treated with NaHCO$_3$ (1.60 g, 19 mmol) and diphenylphosphoryl azide (1.73 mL, 7.98 mmol) at 0° C. and stirred with slow warming to room temperature over 72 h. The reaction mixture was evaporated under vacuum and the residue was purified by flash chromatography (silica gel, 75% ethyl acetate/hexane) to give the title compound (25) (540 mg, 44%). Compound (25): $^1$H NMR (CDCl$_3$) δ 1.47 (s, 9H), 3.50–4.23 (m, 8H), 7.03–7.57 (m, 5H); MS (DCI/NH$_3$) m/e 319 (M+H)$^+$.

f) 1-Phenyl-2,4-dioxo-3-(carbobenzyloxy)methyl-5-[carbo(t-butyloxy)] methyl-hexahydro-1,5-diazepine (26).

A solution of 1-phenyl-2,4-dioxo-5-[carbo(t-butyloxy)] methyl-hexahydro-1,5-diazepine (25) (1.98 g, 6.22 mmol) in a mixture of tetrahydrofuran (30 mL) and hexamethylphosphoramide (10 mL) was cooled to −78° C. and treated with 0.5M potassium bis (trimethylsilyl) amide (13.5 mL) for 20 min. Iodobenzyl acetate (3.46 g, 12.4 mmol) was added and the reaction brought to room temperature over 2 h. The reaction mixture was quenched with saturated NH$_4$Cl (aqueous) followed by 1N HCl and then extracted with ethyl acetate. The combined organic extracts were washed with saturated NaCl (aqueous), dried over anhydrous MgSO$_4$, filtered and evaporated at reduced pressure. The residue was purified by flash chromatography (silica gel, 50% ethyl acetate/hexane) to give the title compound (26) (1.33 g, 46%). Compound (26): $^1$H NMR (CDCl$_3$) δ 1.43 (s, 9H), 3.13 (d, 2H, J=7.5 Hz), 3.33–4.83 (m, 7H), 5.13 (s, 2H), 7.10–7.47 (m, 10H); MS (DCI/NH$_3$) m/e 467 (M+H)$^+$.

g) 1-Phenyl-2,4-dioxo-3-(carbobenzyloxy)methyl-5-(carboxyamido)methyl-hexahydro- 1,5-diazepine (27).

Compound (26) was dissolved in methylene chloride and was treated with trifluoroacetic acid (60 mL) at room temperature for 3 h. The reaction mixture was evaporated at reduced pressure and the residue was evaporated from a mixture of toluene and chloroform to remove any trace of water. The resulting acid was dissolved in tetrahydrofuran (60 mL), cooled to −20° C. and treated with N-methylmorpholine (747 μL, 6.8 mmol) and ethyl chloroformate (650 μL, 6.8 mmol) for 30 min. The reaction mixture was then treated with a mixture of saturated NH$_4$OH (aqueous) (4.5 mL) and tetrahydrofuran (45 mL) and warmed over 1 h to room temperature. The reaction mixture was then poured into cold 3N HCl and extracted with ethyl acetate. The combined organic extracts were dried over anhydrous MgSO$_4$, filtered and evaporated at reduced pressure. The residue was purified by flash chromatography (silica gel, 5% methanol/chloroform) to give the title compound (27) (850 mg, 2.08%). Compound (27): $^1$H NMR (CDCl$_3$) δ 3.10 (d, 2H, J=7.5 Hz), 3.50–4.00 (m, 3H), 4..03 (s, 2H), 4.20–4.83 (m, 2H), 5.10 (s, 2H), 7.07–7.50 (m, 12H); MS (DCI/NH$_3$) m/e 410 (M+H)$^+$.

h) 1-Phenyl-2,4-dioxo-3-(carbobenzyloxy)methyl-5-[t-butyloxycarbonyl-aminomethyl]-hexahydro-1,5-diazepine (28).

A solution of compound (27) in a mixture of acetonitrile and water (4:1, 80 mL) was treated with [bis(trifluoroacetoxy)iodo]-benzene (1.8 g, 4.04 mmol) at room temperature for 5 h. The reaction mixture was evaporated at reduced pressure and the residue was evaporated from toluene (2×) at reduced pressure. The resulting material was dissolved in methylene chloride and was treated with di-t-butyl dicarbonate (913 mg, 4.14 mmol) and triethylamine (585 μL, 4.14 mmol) at room temperature for 18 h. The reaction mixture was evaporated at reduced pressure and the residue was purified by flash chromatography (silica gel, 30–50% ethyl acetate/hexane) to give the title compound (28) (347 mg, 35%). Compound (28): $^1$H NMR (CDCl$_3$) δ 1.40 (s, 9H), 3.10 (d, 2H, J=7.5 Hz), 3.60–4.83 (m, 7H), 5.15 (s, 2H), 5.70 (br t, 1H, J=7.5 Hz), 7.10–7.53 (m, 10H); MS (FAB) m/e 482 (M+H)$^+$.

i) 1-Phenyl-2,4-dioxo-3-(carbobenzyloxy)methyl-5-[t-butyloxycarbonyl-(N-methyl-tosyl-arginyl)-aminomethyl]-hexahydro- 1,5-diazepine (29).

Compound (28) was treated with 4N HCl in dioxane at room temperature for 1.5 h. The reaction mixture was then evaporated at reduced pressure and the residue was evaporated from toluene to remove traces of water and HCl. The resulting material was dissolved in N,N-dimethylformamide and the pH was adjusted to 7 (moist pH paper) with triethylamine. This solution was then treated with Boc-N$^α$-Me-Arg(Tos)-OH (143 mg, 0.327 mmol), 1-hydroxybenzotriazole (44.2 mg, 0.327 mmol) and N,N-dicyclohexylcarbodiimide (67.4 mg, 0.327 mmol), and the resulting mixture was stirred at room temperature for 16 h. The reaction mixture was evaporated under vacuum and the residue was purified twice by flash chromatography (silica gel, 3% methanol/chloroform; silica gel, 75% ethyl acetate/hexane)

to give the title compound (29) (123 mg, 49%) as an inseparable mixture of two diastereomers. Compound (29): $^1$H NMR (CDCl$_3$) δ 1.03–1.99 (m, 14H), 2.37 (s, 3H), 2.58–3.32 (m, 8H), 3.55–4.87 (m, 7H), 5.03–5.16 (m, 2H), 6.16–6.49 (m, 1H), 6.91–7.38 (m, 14H), 7.61–7.78 (m, 2H); MS (ES) m/e 806 (M+H)$^+$.

j) 1-Phenyl-2,4-dioxo-3-(carbobenzyloxy)methyl-5-[(N-acetyl-N-methyl-tosyl-arginyl)aminomethyl]-hexahydro-1,5-diazepine (30).

Compound (29) was treated with 4N HCl in dioxane at room temperature for 3 h. The reaction mixture was evaporated at reduced pressure and the residue was evaporated from toluene to remove any trace of water. The material from above was dissolved in N,N-dimethylformamide (5 mL) and treated with triethylamine (55.6 μL, 0.399 mmol) and acetyl chloride (29 μL, 0.399 mmol) at room temperature for 24 h. The reaction mixture was evaporated under vacuum and the residue was purified by flash chromatography (silica gel, 3% methanol/chloroform; silica gel, 2–10% methanol/chloroform) to give the title compound (30) (102 mg, 89%) as an inseparable mixture of two diastereomers. Compound (30): MS (ES) m/e 748 (M+H)$^+$.

k) 1-Phenyl-2,4-dioxo-3-carboxymethyl-5-[(N-acetyl-N-methylarginyl)-aminomethyl] -hexahydro-1,5-diazepine (31).

Compound (30) (140 mg, 0.192 mmol) from above was dissolved in dichloromethane, transferred to a HF vessel and the solvent evaporated under a stream of argon. Anhydrous HF (10 mL) was condensed into the vessel at −78° C. and the reaction mixture stirred for 1 h at 0° C. The HF was evaporated at reduced pressure and the residue taken into 10% acetic acid (aqueous) and lyophilized to give a crude product (78 mg). A portion of the crude product (32 mg) was dissolved in aqueous acetonitrile and purified by repeated runs on a semi-preparative reverse phase hplc column [5μ IBM ODS column, 10×250 mm, 85:15 water-0.1% trifluoroacetic acid:acetonitrile- 0.1% trifluoroacetic acid] to give, after evaporation and lyophilization from 1% acetic acid, the title compound (31) (9 mg) as an inseparable mixture of two diastereomers. Compound (31): MS (ES) m/e 504 [M+H]$^+$; HPLC k' 1.54 [5μ Apex-ODS, UV detection at 220 nm, 80:20 water-0.1% trifluoroacetic acid:acetonitrile-0.1% trifluoroacetic acid]; HPLC k' 3.43 [5μ Apex-ODS, UV detection at 220 nm, gradient, A: water-0.1% trifluoroacetic acid, B: acetonitrile-0.1% trifluoroacetic acid, 10–50% B during 20 mini; TLC R$_f$ 0.17 (silica gel, 4:1:1 butanol:acetic acid:water); TLC R$_f$ 0.37 (silica gel, 1:1:1:1 butanol:acetic acid:water:ethyl acetate).

EXAMPLE 4

One method to enhance the separation of the diastereomers to insert a chiral auxiliary in close proximity to the acidic side chain of the azepine. For example, the synthesis of 1-phenyl-2-oxo-3-(carbobenzyloxy)methyl-5-[ benzoyl-(N-methyl-tosyl-arginyl)-aminomethyl]-2,3,6,7-tetrahydro-1H-azepine (17) is repeated as in Example 1 except that iodo (R)-α-methylbenzyl acetate is used in place of benzyl bromide in the alkylation (step f). The resulting diastereomers can then be separated at any subsequent step before final removal of the auxiliary (step 1) with the only requirement being that the resolved center on the azepine be stable to racemization during subsequent steps in the synthesis. Separation of isomers late in the synthetic sequence is prefered for this reason. Final deprotection of each diastereomer yields both 1-phenyl-2-oxo-3-(R)-(carboxy)methyl- 5-[benzoyl-(N-methyl-tosyl-arginyl)aminomethyl] -2,3,6,7-tetrahydro-1H-azepine and 1-phenyl-2-oxo- 3-(S)-(carboxy)methyl-5-[benzoyl-(N-methyl-tosyl-arginyl)aminomethyl] -2,3,6,7-tetrahydro-1H-azepine.

EXAMPLE 5

Parenteral Dosage Unit Composition

A preparation which contains 20 mg of the compound of Example 1 as a sterile dry powder is prepared as follows: 80 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 6

Oral Dosage Unit Composition

A capsule for oral administration is prepared by mixing and milling 150 mg of the compound of Example 3 with 225 mg of lactose and 15 mg of magnesium stearate. The resulting powder is screened and filled into a hard gelatin capsule.

EXAMPLE 7

Oral Dosage Unit Composition

A tablet for oral administration is prepared by mixing and granulating 40 mg of sucrose, 300 mg of calcium sulfate dihydrate and 100 mg of the compound of Example 3 with a 10% gelatin solution. The wet granules are screened, dried, mixed with 20 mg starch, 10 mg talc and 6 mg stearic acid; and compressed into a tablet.

The above description fully discloses how to make and use this invention. This invention, however, is not limited to the precise embodiments described herein, but encompasses all modifications within the scope of the claims which follow.

What is claimed is:

1. A compound of the formula:

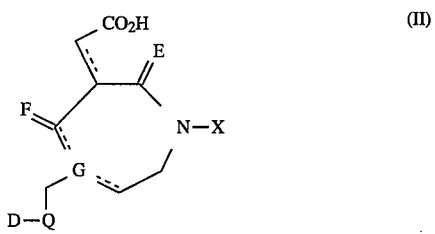

wherein:

Q is NR' or O;

D is

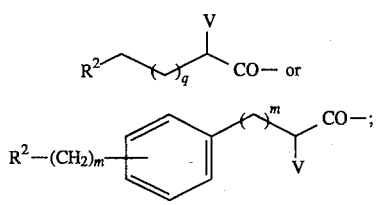

E and F are (H,H), O or S;

G is N or C;

V is H, R', SR', A-B-O or A-B-NR';

A is H, R', $(CH_2)_nAr$, $R_1CO$, $R_1OCO$, $R_1OCH(R_{1'})CO$, $R_1NHCH(R_{1'})CO$, $R_1SCH(R_{1'})CO$, $R_1SO_2$ or $R_1SO$;

$R_1$ and $R_{1'}$ are H, $C_{1-5}$alkyl, $C_{3-7}$cycloalkyl, aryl or aryl substituted by one or two $C_{1-5}$alkyl, trifluoromethyl, hydroxy, $C_{1-5}$alkoxy or halogen groups;

$R^2$ is $N(R')_2$, NR'C(=O)NHR', C(=NR')NHR' or NR'C(=NR')NHR';

B is absent, Arg, HArg, $(Me_2)$Arg, $(Et_2)$Arg, Ala, Gly, His, Abu or an α-R' substituted derivative thereof, or Pro;

X is R", $CHRCH_2$-Y-Z or CHRCO-Y-Z;

Y is absent or a D- or L- amino acid chosen from Tyr, (Alk)Tyr, Phe, (4'W)Phe, HPhe, Phg, Trp, His, Ser, (Alk)Ser, Thr, (Alk)Thr, Cys, (Alk)Cys, Pen, (Alk)Pen, Ala, Val, Nva, Met, Leu, Ile, Nle and Nal;

Z is R" or OR", NR'R" or R";

R is H, $C_{1-6}$alkyl, $(CH_2)_n$Het, $(CH_2)_n$CONHR', $(CH_2)_n$NR'R', $(CH_2)_n$NC=N-NR', $(CH_2)_n$OR' or $(CH_2)_n$SR' or $(CH_2)_n$Ar;

R' is H, $C_{1-4}$ alkyl or $(CH_2)_n$Ar;

R" is H, $C_{1-6}$alkyl, $C_{3-7}$cycloalkyl, amino, Ar, $(CHR')_n(CH_2)_n$-Ar, $C_{3-7}$cycloalkyl-Ar, Het, $(CH_2)_n$Het or $C_{3-7}$cycloalkyl-Het;

Ar is phenyl or naphthyl optionally substituted by one or two $C_{1-5}$alkyl, $C_{1-5}$alkoxy, $C_{1-5}$alkylthio, $CO_2R'$, $CON(R')_2$, hydroxy, halogen, trifluoromethyl, amino or nitro groups.

Het is pyridyl, indolyl, imidazolyl or thienyl substituted by one or two $C_{1-4}$alkyl, $CO_2R'$, $CON(R')_2$, OR' or SR';

-- is a single or double bond;

m is 0 to 2;

n is 0 to 3;

p is 1 to 3;

q is 1 to 4; and pharmaceutically acceptable salts thereof.

2. A compound according to claim 1 wherein Q is NH.

3. A compound according to claim 1 wherein D is

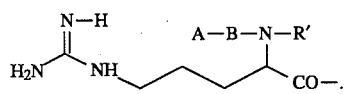

4. A compound according to claim 3 wherein B is absent.

5. A compound according to claim 4 wherein A is benzoyl.

6. A compound according to claim 1 wherein X is phenyl.

7. A compound according to claim 1 which is:

1-phenyl-2-oxo-3-carboxymethyl-5-[(N-benzoyl-N-methylarginylamino)methyl] -2,3,6,7-tetrahydro-1H-azepine; or 1-phenyl-2-oxo-3-carboxymethyl-5-[(N-acetyl-N-methylarginylamino)methyl] -2,3,6,7-tetrahydro-1H-azepine.

8. A pharmaceutical composition which comprises a compound according to claim 3 and a pharmaceutically acceptable carrier.

9. A method for effecting inhibition of platelet aggregation which comprises administering to a mammal in need thereof, a compound according to claim 1.

10. A method for effecting thrombolysis and inhibiting reocclusion of an artery or vein in a mammal which comprises internally administering a fibrinolytic agent and a compound according to claim 1.

11. A method according to claim 10 in which the fibrinolytic is anistreplase, streptokinase (SK), urokinase (UK), pro-urokinase (pUK) or tissue plasminogen activator (tPA) or a mutant or derivative thereof.

12. A kit for use in a method for effecting thrombolysis and inhibiting reocclusion of an artery in a mammal which comprises, in separate containers, an effective amount of a fibrinolytic agent and a compound according to claim 1.

13. A kit according to claim 12 in which the fibrinolytic agent is anistreplase, streptokinase (SK), urokinase (UK), pro-urokinase (pUK), tissue plasminogen activator (tPA) or a mutant or derivative thereof.

14. A process for preparing a compound of the formula (II):

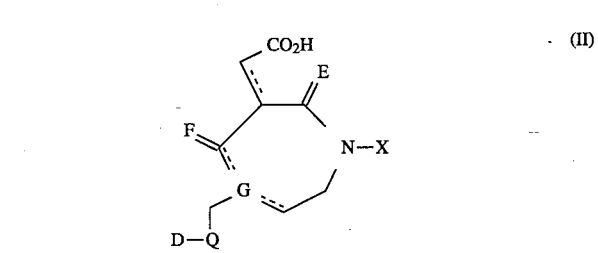

wherein D, E, Q and X are as defined in claim 1, which comprises, a) reacting a compound of the formula (VI):

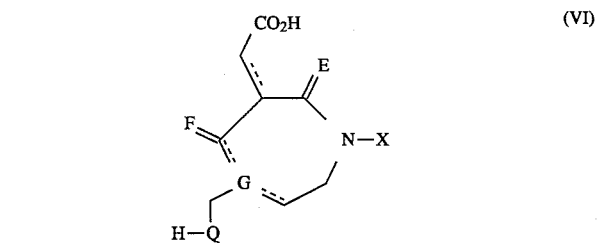

wherein X is as defined in claim 1 with any reactive groups protected; Q and E are as defined in claim 1; and $R_p$ is a carboxyl protecting group;

with a carboxylic acid of the formula D-OH and a coupling reagent, and b) removing any protecting groups.

15. A method of treating congestive heart failure comprising administering a compound according to claim 1.

16. A pharmaceutical composition which comprises a compound according to claim 1 and a pharmaceutically acceptable carrier.

* * * * *